US012716853B2

(12) United States Patent
Yurugi et al.

(10) Patent No.: US 12,716,853 B2
(45) Date of Patent: Aug. 25, 2026

(54) X-RAY INSPECTION APPARATUS

(71) Applicant: ISHIDA CO., LTD., Kyoto (JP)

(72) Inventors: Futoshi Yurugi, Ritto (JP); Kota Tominaga, Ritto (JP); Shojiro Kita, Ritto (JP); Satoshi Onda, Ritto (JP)

(73) Assignee: ISHIDA CO., LTD., Kyoto (JP)

( * ) Notice: Subject to any disclaimer, the term of this patent is extended or adjusted under 35 U.S.C. 154(b) by 140 days.

(21) Appl. No.: 18/923,777

(22) Filed: Oct. 23, 2024

(65) Prior Publication Data

US 2025/0137944 A1 May 1, 2025

(30) Foreign Application Priority Data

Oct. 31, 2023 (JP) ................................ 2023-186660

(51) Int. Cl.
*G01N 23/04* (2018.01)
*G01N 23/083* (2018.01)
(Continued)

(52) U.S. Cl.
CPC ............ *G01N 23/18* (2013.01); *G01N 23/04* (2013.01); *G01N 23/083* (2013.01); *G01N 33/02* (2013.01); *H05G 1/46* (2013.01); *H05G 1/58* (2013.01); *G01N 2223/1016* (2013.01); *G01N 2223/204* (2013.01); *G01N 2223/3032* (2013.01); *G01N 2223/306* (2013.01); *G01N 2223/413* (2013.01);
(Continued)

(58) Field of Classification Search
None
See application file for complete search history.

(56) References Cited

U.S. PATENT DOCUMENTS 7,787,593 B2 * 8/2010 Klein .................... G01N 23/22 378/114
8,027,427 B2 * 9/2011 Basu .................... G01N 23/046 378/20
(Continued)

FOREIGN PATENT DOCUMENTS

JP 2021-156635 A 10/2021
JP 6979185 B2 12/2021
(Continued)

OTHER PUBLICATIONS

1 Extended Search Report in the corresponding European Patent Application No. 24209120.5 dated Feb. 28, 2025.

*Primary Examiner* — Thomas R Artman
(74) *Attorney, Agent, or Firm* — Spencer Fane LLP

(57) ABSTRACT

An X-ray inspection apparatus includes a conveying unit configured to convey an article, an irradiation unit configured to irradiate the article conveyed by the conveying unit with X-rays, a sensor unit in which detecting elements are arranged in a planar shape, an image generation unit configured to read detection results output from at least some of the detecting elements and generate an image, and a mode switching unit configured to switch an operation mode between a first mode in which a first electric power is supplied to the irradiation unit and a second mode in which a second electric power less than the first electric power is supplied to the irradiation unit, where the mode switching unit changes, when switching the operation mode from the first mode to the second mode, a read frequency at which the image generation unit reads the detection results.

7 Claims, 4 Drawing Sheets

(51) Int. Cl.

| | |
|---|---|
| ***G01N 23/18*** | (2018.01) |
| ***G01N 33/02*** | (2006.01) |
| ***H05G 1/46*** | (2006.01) |
| ***H05G 1/58*** | (2006.01) |
| *H05G 1/54* | (2006.01) |

(52) U.S. Cl.

CPC . *G01N 2223/423* (2013.01); *G01N 2223/618* (2013.01); *G01N 2223/643* (2013.01); *G01N 2223/646* (2013.01); *G01N 2223/652* (2013.01); *H05G 1/54* (2013.01)

(56) References Cited

U.S. PATENT DOCUMENTS

| | | | | |
|---|---|---|---|---|
| 8,265,223 | B2 | 9/2012 | Proksa | |
| 9,528,948 | B2 * | 12/2016 | Lüghausen | G01N 23/04 |
| 12,222,301 | B2 * | 2/2025 | Iwakawa | G01N 23/04 |
| 12,343,189 | B2 * | 7/2025 | Iwakawa | A61B 6/482 |
| 12,504,387 | B2 * | 12/2025 | Yoshida | G01N 23/04 |
| 12,590,909 | B2 * | 3/2026 | Sugimoto | G01N 23/04 |
| 2007/0280413 | A1 * | 12/2007 | Klein | G01N 23/22 378/45 |
| 2011/0051886 | A1 * | 3/2011 | Basu | G01N 23/046 378/57 |
| 2011/0135052 | A1 * | 6/2011 | Proksa | A61B 6/032 378/19 |
| 2014/0328463 | A1 | 11/2014 | Lüghausen et al. | |
| 2023/0284991 | A1 * | 9/2023 | Iwakawa | A61B 6/482 |
| 2024/0310301 | A1 * | 9/2024 | Yoshida | G01N 23/04 |
| 2024/0310302 | A1 * | 9/2024 | Sugimoto | G01N 23/04 |
| 2025/0116616 | A1 * | 4/2025 | Kanai | G01N 23/04 |
| 2025/0123222 | A1 * | 4/2025 | Yurugi | H05G 1/54 |
| 2025/0137944 | A1 * | 5/2025 | Yurugi | G01N 23/18 |
| 2025/0180773 | A1 * | 6/2025 | Ikeda | G06T 7/0004 |
| 2026/0023034 | A1 * | 1/2026 | Yurugi | G01N 23/04 |

FOREIGN PATENT DOCUMENTS

| | | |
|---|---|---|
| JP | 2023-132587 A | 9/2023 |
| JP | 2024-129940 A | 9/2024 |

* cited by examiner

X-RAY INSPECTION APPARATUS

CROSS REFERENCE TO RELATED APPLICATIONS

This application claims the benefit of priority to Japanese Patent Application Number 2023-186660 filed on Oct. 31, 2023. The entire contents of the above-identified application are hereby incorporated by reference.

TECHNICAL FIELD

The disclosure relates to an X-ray inspection apparatus.

BACKGROUND

In the related art, an inspection apparatus using electromagnetic waves such as X-rays is used as an apparatus for inspecting objects to be inspected (articles) such as foodstuffs and pharmaceuticals. For example, an article inspection apparatus disclosed in JP 2021-156635 A is provided with an irradiation unit that irradiates a moving object to be inspected with radially spreading electromagnetic waves, and a detection unit that detects electromagnetic waves affected by the object to be inspected by detecting elements.

SUMMARY

In the article inspection apparatus as described above, there is a tendency that the irradiation unit which is an output source of the electromagnetic waves deteriorates at the earliest. To suppress the deterioration of the irradiation unit, it is conceivable to suppress the output of the electromagnetic waves. However, when the output of the electromagnetic waves is simply suppressed, the detection of the electromagnetic waves by the detection unit becomes insufficient, and there is a concern that pass/fail judgement of an object to be inspected may not be accurately conducted.

An object of one aspect of the disclosure is to provide an X-ray inspection apparatus that can perform a satisfactory inspection regardless of suppressing the output of X-rays.

(1) An X-ray inspection apparatus according to one aspect of the disclosure, includes a conveying unit configured to convey an article, an irradiation unit configured to irradiate the article conveyed by the conveying unit with X-rays, a sensor unit in which detecting elements configured to detect the X-rays are arranged in a planar shape, an image generation unit configured to read detection results output from at least some of the detecting elements and generate an image, and a mode switching unit configured to switch an operation mode between a first mode in which a first electric power is supplied to the irradiation unit and a second mode in which a second electric power less than the first electric power is supplied to the irradiation unit, where the mode switching unit changes, when switching the operation mode from the first mode to the second mode, a read frequency at which the image generation unit reads the detection results.

In this X-ray inspection apparatus, when switching the operation mode from the first mode in which the first power is supplied to the irradiation unit to the second mode in which the second power less than the first power is supplied to the irradiation unit, the mode switching unit changes the read frequency at which the image generation unit reads the detection results. For example, it is possible to extend the exposure time of the detecting elements during a predetermined period by reducing the read frequency of the detection results, when the first mode is switched to the second mode. This enables satisfactory detection results of the X-rays to be output from each detecting element, even when the output of the X-rays emitted from the irradiation unit is weakened in the second mode. Thus, by using the above X-ray inspection apparatus, a satisfactory inspection can be performed regardless of suppressing the output of X-rays.

(2) In the X-ray inspection apparatus according to above (1), the sensor unit may be configured to detect the X-rays by a photon counting method. In this case, the contrast of the image generated by the image generation unit can be improved.

(3) In the X-ray inspection apparatus according to above (1) or (2), the second electric power may be any multiple less than 1 time of the first power. In this case, the power consumption of the X-ray inspection apparatus can be satisfactorily reduced.

(4) In the X-ray inspection apparatus according to above (3), when switching the operation mode from the first mode to the second mode, the mode switching unit may multiply the read frequency by any multiple less than 1 time. In this case, satisfactory detection results of the X-rays can be surely output from each sensor.

(5) In the X-ray inspection apparatus according to any one of (1) to (4), when the first mode is switched to the second mode, the sensor unit may change the number of detecting elements that operate among the detecting elements. In this case, since the detecting element with an insufficient exposure time hardly exists, an unclear image is less likely to be generated.

(6) In the X-ray inspection apparatus according to (5), when the first mode is switched to the second mode, a change rate of the read frequency may be the same as a ratio of the detecting elements that operate among the detecting elements. In this case, satisfactory detection results of the X-rays can be surely output from operating detecting elements.

(7) The X-ray inspection apparatus according to any one of above (1) to (6), may further include a determination unit configured to determine whether a foreign matter is present in the article including a food, on the basis of the image. In this case, the determination unit can satisfactorily determine whether a foreign matter is present even when the X-ray output is suppressed.

One aspect of the disclosure can provide an X-ray inspection apparatus that can perform a satisfactory inspection regardless of suppressing the output of X-rays.

DESCRIPTION OF EMBODIMENTS

A preferred embodiment of the disclosure will now be described in detail with reference to the accompanying drawings. Note that in the description of the drawings, the same or equivalent elements are denoted by the same reference signs, and duplicate descriptions will be omitted.

Figure 1:
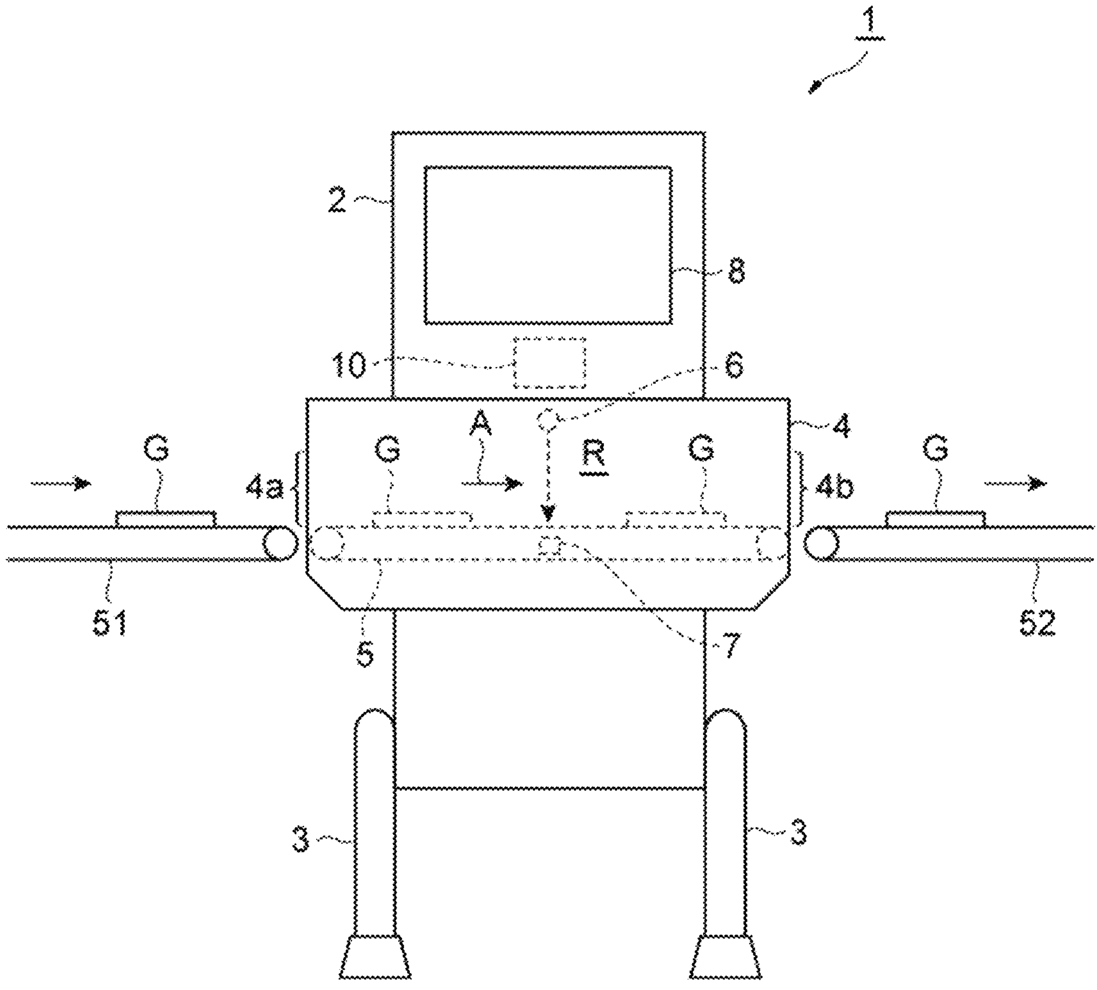
FIG. 1 is a configuration diagram of an X-ray inspection apparatus according to an embodiment.

As illustrated in FIG. 1, an X-ray inspection apparatus 1 includes a main body 2, a support leg 3, a shield box 4, a conveying unit 5, an X-ray irradiation unit 6, a sensor unit 7, a display operation unit 8, and a control unit 10. The X-ray inspection apparatus 1 generates X-ray transmission images of an article G while conveying the article G, and inspects the article G on the basis of the X-ray transmission images. The article G before inspection is carried into the X-ray inspection apparatus 1 by a supply conveyor 51. The article G after inspection is carried out from the X-ray inspection apparatus 1 by a delivery conveyor 52.

The main body 2 accommodates the control unit 10 or the like. The support leg 3 supports the main body 2. The shield box 4 is provided in the main body 2. The shield box 4 is a housing for preventing leakage of X-rays (electromagnetic waves) to the outside. Inside the shield box 4, an inspection chamber R is provided in which the inspection of article G by X-rays is performed. A supply port 4*a* and a delivery port 4*b* are formed in the shield box 4. The article G before the inspection is carried from the supply conveyor 51 to the inspection chamber R through the supply port 4*a*. The article G after the inspection is carried from the inspection chamber R to the delivery conveyor 52 through the delivery port 4*b*.

The conveying unit 5 is a member for conveying the article G, and is arranged extending through the center of the shield box 4. The conveying unit 5 conveys the article G along a conveyance direction A from the supply port 4*a* to the delivery port 4*b* via the inspection chamber R. The speed (conveyance speed) at which the article G is conveyed by the conveying unit 5 is set by the control unit 10, for example. The conveying unit 5 is, for example, a belt conveyor stretched between the supply port 4*a* and the delivery port 4*b*. Note that the conveying unit 5 may project outward from the supply port 4*a* and the delivery port 4*b*.

Figure 2:
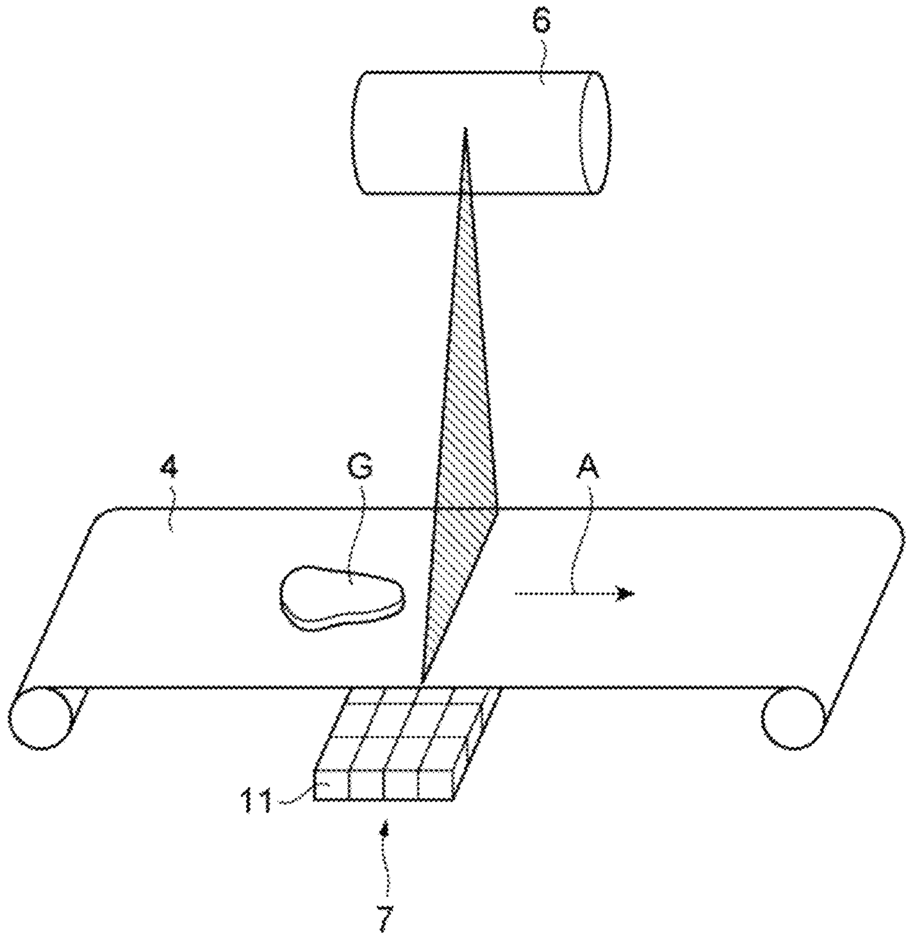
FIG. 2 is a schematic configuration diagram of the interior of a shield box illustrated in FIG. 1.

As illustrated in FIGS. 1 and 2, the X-ray irradiation unit 6 is an electromagnetic waves irradiation unit arranged in the shield box 4, and irradiates the article G conveyed by the conveying unit 5 with X-rays. The X-rays include X-rays of various energy regions from low energy (long wavelength) to high energy (short wavelength). Thus, the X-ray irradiation unit 6 irradiates the article G conveyed by the conveying unit 5 with X-rays of a plurality of energy regions. X-ray irradiation (i.e., idling of X-ray irradiation unit 6) by the X-ray irradiation unit 6 may be performed after the activation of the X-ray inspection apparatus 1 and before the inspection of the article G. Note that "low" and "high" in the above-described low energy and high energy indicate "low" and "high" relatively among a plurality of energy regions of the X-rays emitted from the X-ray irradiation unit 6, and do not indicate a specific range.

In the present embodiment, the power (in particular, current) supplied to the X-ray irradiation unit 6 can be changed manually or automatically. By changing the power, the output of the X-rays emitted to the article G can be changed. For example, when the sensor unit 7 is irradiated with excessive X-rays, the power supplied to the X-ray irradiation unit 6 is reduced. On the other hand, when the sensor unit 7 is irradiated with an insufficient amount of X-rays, the power supplied to the X-ray irradiation unit 6 is increased. When an operation mode or the like of the X-ray inspection apparatus 1 is manually or automatically set, electric power (particularly, current) supplied to the X-ray irradiation unit 6 may be switched. For example, when a normal mode (first mode) and a power-saving mode (second mode) are included in the operation mode, a first power is supplied to the X-ray irradiation unit 6 in the normal mode, and a second power less than the first power is supplied to the X-ray irradiation unit 6 in the power-saving mode. The second power is, for example, a reciprocal multiple of a natural number of the first power, but not limited to this. For example, the second power may be any multiple (0.9 times, 0.85 times, 0.6 times, 0.3 times, or the like) less than 1 time of the first power. In the power-saving mode, the article G is inspected in a state where the electric power supplied to the X-ray inspection apparatus 1 is reduced as compared with in the normal mode. In the present specification, a natural number is an integer of 2 or more.

The sensor unit 7 is a sensor unit that detects electromagnetic waves. The sensor unit 7 is arranged in the shield box 4 at a position facing the X-ray irradiation unit 6 in the vertical direction. The sensor unit 7 includes detecting elements 11 arranged in a planar shape (two-dimensional). The detecting elements 11 are arranged in a direction (width direction) orthogonal to at least the conveyance direction A of the conveying unit 5 and the vertical direction. A line sensor may be configured by some of the detecting elements 11 in the sensor unit 7. For example, line sensors extending along the width direction may be arranged side by side in the conveyance direction A in the sensor unit 7. In this case, each of the line sensors includes detecting elements 11 arranged along the width direction. Note that unless otherwise mentioned below, the detecting elements 11 correspond to all the detecting elements 11 included in the sensor unit 7.

In the present embodiment, the sensor unit 7 is a direct conversion type detection unit that can detect X-rays by a photon counting method. The detecting element 11 is, for example, a sensor (multi-energy sensor) that detects X-rays in each of a plurality of energy regions transmitted through the article G, and the sensor unit 7 may be a Time Delay Integration sensor (TDI sensor). The detecting element 11 includes, for example, a photon detection type sensor such as a CdTe semiconductor detector. In the detecting element 11, for example, an electron-hole pair is generated when an X-ray photon arrives. A process for counting photons (photon counting) is performed on the basis of the energy (photon energy) obtained at this time. The counting process is performed, for example, by the sensor unit 7 or by a calculation unit (not illustrated) included in the detecting element 11. The result of the counting process (detection result) of each detecting element 11 by the calculation unit is output to the control unit 10 at a predetermined time interval, for example. The predetermined time interval is also referred to as a read interval or a delay time, and can be appropriately changed by the control unit 10 (details will be described below).

Each detecting element 11 of the sensor unit 7 may classify the photon energy of X-rays, which is detected on the basis of any threshold, into two or more energy regions. In this case, the sensor unit 7 can perform photon counting in each energy region. Any threshold is, for example, one or more values (in keV) set by the control unit 10. Any threshold may be set, for example, by the method described in JP 2023-132587 A, or by using a following brightness level.

Figure 3:
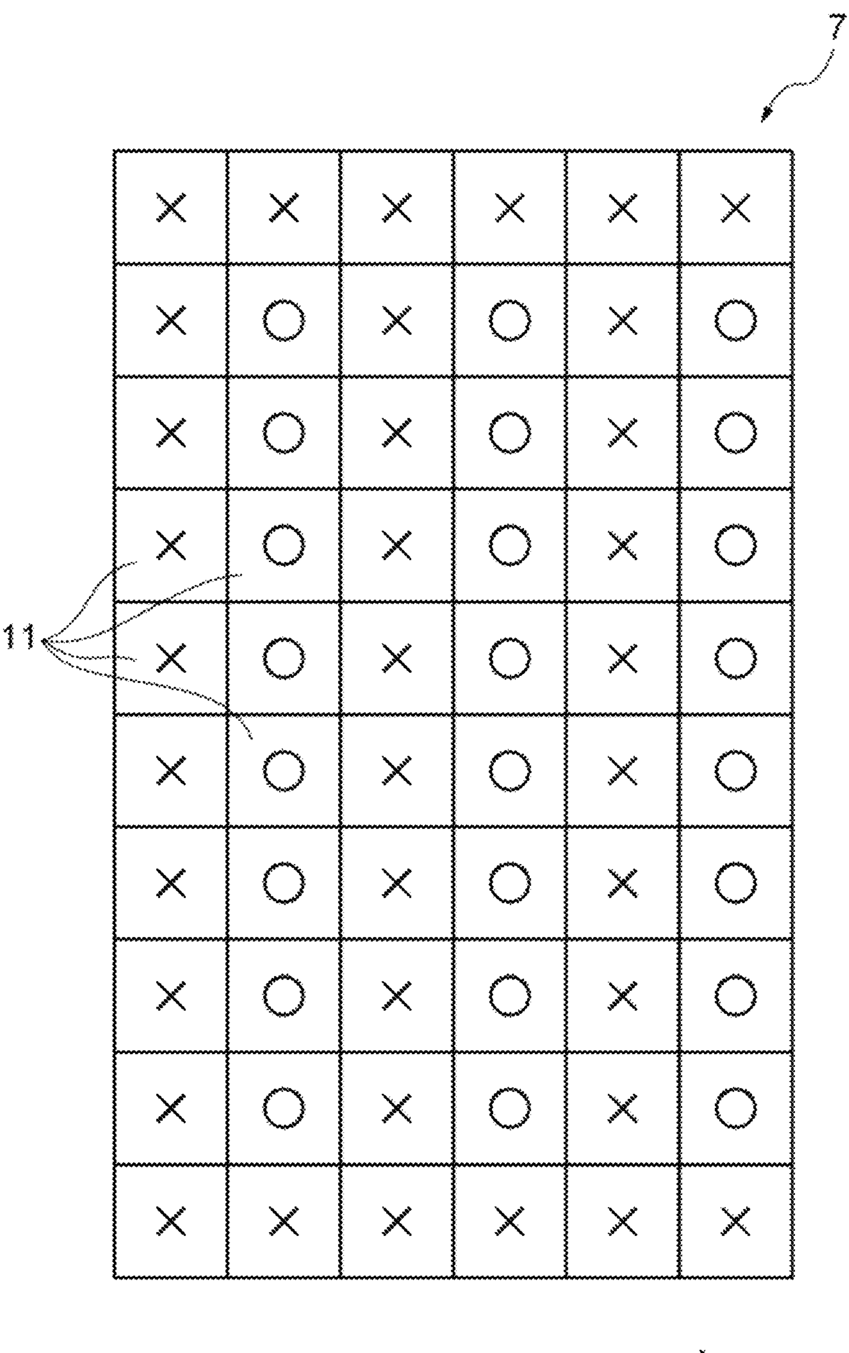
FIG. 3 is a schematic diagram illustrating detecting elements in operation and detecting elements not used for image generation.

The sensor unit 7 may change the number of operating detecting elements 11 on the basis of the conveyance speed of the conveying unit 5, the operation mode of the X-ray inspection apparatus 1, or the like. FIG. 3 is a schematic diagram illustrating operating detecting elements, and detecting elements not used for image generation. FIG. 3 illustrates some of the detecting elements 11 included in the sensor unit 7, and "○" is added to each of operating detecting elements 11 (detecting elements 11 used for image generation), and "x" is added to each of detecting elements 11 not used for image generation. For example, when the conveyance speed is excessive and satisfactory detection results cannot be output from all the detecting elements 11, or when the control unit 10 switches the operation mode of the X-ray inspection apparatus 1 from the normal mode to the power-saving mode, the sensor unit 7 limits the number of operating detecting elements 11 as illustrated in FIG. 3. Thus, satisfactory detection results can be output from all the operating detecting elements 11. The detecting elements 11 to be limited are selected according to predetermined rules, patterns, or the like. The rules, patterns, or the like may be appropriately changed depending on the type of article G, the total operation time of the X-ray inspection apparatus 1, or the like. For example, when the X-ray inspection apparatus 1 operates in the second mode, the operating detecting elements 11 may be always the same or may be changed depending on the cumulative operation time of the X-ray inspection apparatus 1. On the other hand, when the sensor unit 7 limits the number of operating detecting elements 11 and when the conveyance speed is no longer excessive, the sensor unit 7 releases the limit on the number of operating detecting elements 11. This increases the number of operating detecting elements 11. Note that when the line sensors are arranged in the sensor unit 7, the sensor unit 7 may limit the number of operating line sensors. In this case, control of the detecting elements 11 by the sensor unit 7 can be simplified. When the X-ray inspection apparatus 1 operates in the second mode, every other line sensor of the line sensors included in the sensor unit 7 in the conveyance direction A may operate or every two line sensors may operate, for example. Note that in the present embodiment, the sensor unit 7 changes the number of operating detecting elements 11, but not limited to this. The number of operating detecting elements 11 may be changed manually, for example.

When the X-ray inspection apparatus 1 is activated, sensitivity correction (calibration) of the sensor unit 7 may be performed. In the sensitivity correction, a brightness level of each detecting element 11 is acquired on the basis of the X-rays that have not passed through the article G. The brightness level is a count number of photons detected when the X-rays not passing through the article G are incident on the sensor unit 7. Sensitivity correction of the sensor unit 7 corresponds to correction of output differences between the detecting elements 11 included in the sensor unit 7. From the viewpoint of shortening the start-up time of the X-ray inspection apparatus 1, in the sensitivity correction, X-ray irradiation by the X-ray irradiation unit 6 may be started simultaneously with the start of X-ray detection by the sensor unit 7. Note that the sensitivity correction of the sensor unit 7 is performed by the method described in JP Application No. 2023-39353, for example.

As illustrated in FIG. 1, the display operation unit 8 is a member (display unit) provided in the main body 2. The display operation unit 8 displays various information and receives input operations of various conditions from the outside. The display operation unit 8 is, for example, a liquid crystal display and displays an operation screen as a touch panel. In this case, the operator can input various conditions via the display operation unit 8. For example, the operator can set the operation mode of the X-ray inspection apparatus 1, the conveyance speed of the conveying unit 5, the power (at least one of current and voltage) supplied to the X-ray irradiation unit 6, the number of operating detecting elements 11, or the like, through the display operation unit 8. The input operation received by the display operation unit 8 is output to the conveying unit 5, the sensor unit 7, the control unit 10, or the like.

The control unit 10 is arranged inside the main body 2. The control unit 10 controls the operation of each unit of the X-ray inspection apparatus 1. The control unit 10 is composed of a Central Processing Unit (CPU), a Read Only Memory (ROM), a Random Access Memory (RAM), or the like. The ROM stores a program for controlling the X-ray inspection apparatus 1, an operation mode of the X-ray inspection apparatus 1, or the like.

Figure 4:
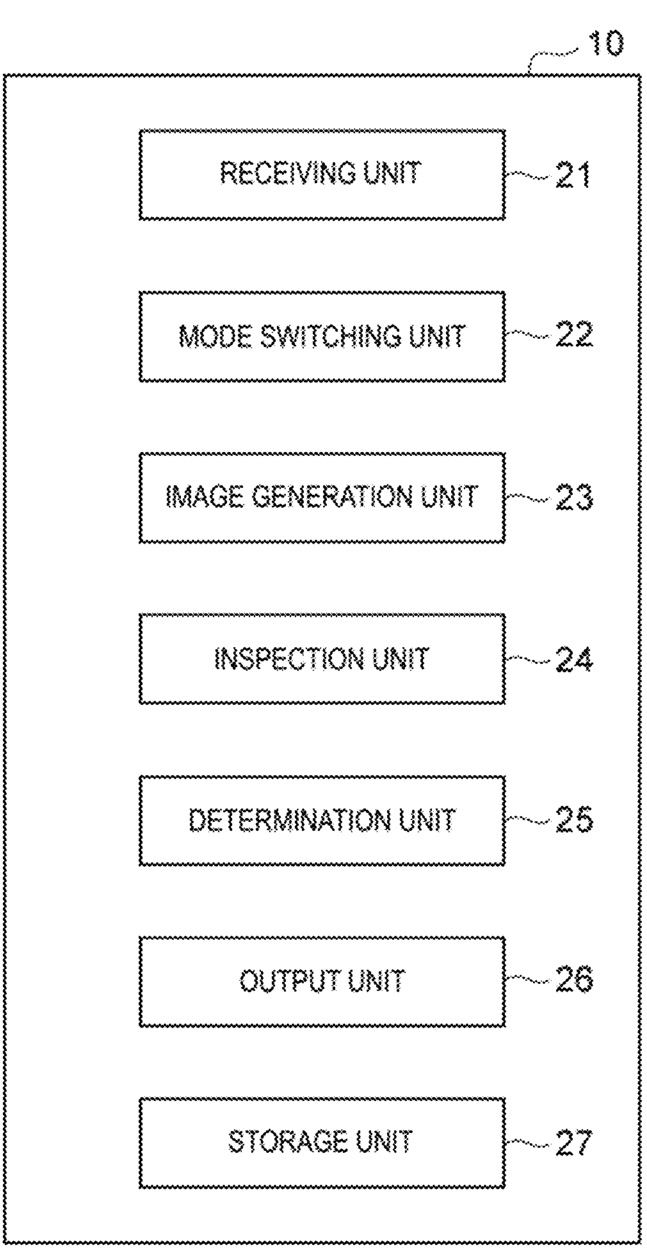
FIG. 4 is a functional configuration diagram of a control unit.

FIG. 4 is a functional configuration diagram of the control unit. As illustrated in FIG. 4, the control unit 10 includes a receiving unit 21, a mode switching unit 22, an image generation unit 23, an inspection unit 24, a determination unit 25, an output unit 26, and a storage unit 27.

The receiving unit 21 receives the input operation received by the display operation unit 8. The receiving unit 21 transmits, for example, a signal (mode designation signal) designating the operation mode of the X-ray inspection apparatus 1 set via the display operation unit 8 to the mode switching unit 22 and the output unit 26. The mode designation signal transmitted to the output unit 26 is output to the sensor unit 7. The receiving unit 21 also receives the detection results output from the sensor unit 7. The receiving unit 21 transmits the received detection results to the image generation unit 23.

The mode switching unit 22 switches the operation mode of the X-ray inspection apparatus 1 to an operation mode according to the mode designation signal. For example, the mode switching unit 22 switches the operation mode between the normal mode in which the first power is supplied to the X-ray irradiation unit 6 and the power-saving mode in which the second power is supplied to the X-ray irradiation unit 6. For example, when switching the operation mode from the normal mode to the power-saving mode, the mode switching unit 22 changes the read frequency (unit: times/hour) at which the image generation unit 23 reads the detection results. The read frequency corresponds to the reciprocal of the above-described read interval. Thus, in the present embodiment, when switching the operation mode from the normal mode to the power-saving mode, the mode switching unit 22 changes the read interval of the detection results by the image generation unit 23.

In the present embodiment, when the mode switching unit 22 switches the operation mode from the normal mode to the power-saving mode, not only the power supplied to the X-ray irradiation unit 6 is reduced, but also the mode switching unit 22 reduces the read frequency at which the image generation unit 23 reads the detection results. This enables the period (X-ray exposure period) during which the detecting elements 11 are exposed to X-rays in the read interval to be extended. The mode switching unit 22 may also change the read frequency at which the image generation unit 23 reads the detection results, when switching the operation mode from the power-saving mode to the normal mode. This makes it difficult for the detecting elements 11 to detect excessive X-rays. In the present embodiment, the mode switching unit 22 multiplies the read frequency by the reciprocal of a natural number when switching the operation mode from the normal mode to the power-saving mode, but not limited to this. For example, when switching the operation mode from the normal mode to the power-saving mode, the mode switching unit 22 may multiply the read frequency by any multiple (e.g., 0.75 times, 0.7 times, 0.6 times, 0.4 times, or the like) less than 1 time. In other words, when switching the operation mode from the normal mode to the power-saving mode, the mode switching unit 22 may multiply the read interval by a natural number, or may multiply the read interval by any multiple (1.25 times, 1.4 times, 1.6 times, 1.75 times, or the like) more than 1 time. Regardless of the change in the read interval, the period required for the counting process by the sensor unit 7, or by the calculation unit included in the detecting element 11 is constant. Thus, regardless of the operation mode of the X-ray inspection apparatus 1, the read interval may be changed such that the ratio of the X-ray exposure period of each detecting element 11 in the read interval becomes a predetermined value or more.

When the mode switching unit 22 switches the operation mode from the normal mode to the power-saving mode, both the change of the read frequency and the change of the number of the operating detecting elements 11 by the sensor unit 7 may be performed. In this case, the change rate of the read frequency may have some relationship with the ratio of the operating detecting elements 11 among all the detecting elements 11 included in the sensor unit 7. For example, the change rate of the read interval may be a reciprocal multiple of the ratio of the operating detecting elements 11 among the detecting elements 11, or may be a ratio other than a reciprocal multiple of the ratio. When the change rate of the read frequency is the same as the ratio of the operating detecting elements 11 among the detecting elements 11, the operation control of the X-ray inspection apparatus 1 can be facilitated.

The image generation unit 23 is mainly composed of, for example, a Graphics Processing Unit (GPU), and develops the detection result signals into a two-dimensional image on a memory. The memory in which the two-dimensional image is developed is, for example, a memory included in the GPU, but not limited to this. The image generation unit 23 reads the detection results output from at least some of the detecting elements 11 included in the sensor unit 7 at the read interval, for example, to generate one or more time delay integral images used for the inspection of the article G. For example, transmission images respectively corresponding to the plurality of energy regions are generated by the image generation unit 23. The image generation unit 23 may generate one or more of difference images from the plurality of transmission images. The image generation unit 23 may use, for example, an image processing algorithm or a program automatically set by machine learning. The image processing algorithm is composed of one image processing filter or a combination of several image processing filters. At least one or more image processing algorithms can be automatically generated from the plurality of image processing filters on the basis of the specifications, inspection conditions or the like of the X-ray inspection apparatus 1 by employing Genetic Algorithms (GA), which are methods realized by applying the mechanism of heredity and evolution in the biological world. At least a part of the image processing algorithms can also be appropriately set by the operator via the display operation unit 8. The program automatically set by machine learning is a predictive model (learned model) generated by machine learning, and an inference program in which parameters (learned parameters) obtained as a result of machine learning are incorporated. Examples of machine learning used in the learned model include neural networks, support vector machines, and genetic algorithms.

The inspection unit 24 inspects the article G on the basis of the images generated by the image generation unit 23. For example, the inspection unit 24 inspects the article G by using the transmission images, the difference images, or the like. The inspection unit 24 may inspect the article G on the basis of both the difference images and the transmission images. During the generation of the difference images by the image generation unit 23, the inspection of the article G based on the transmission images or the like may be performed. The inspection unit 24 inspects, for example, the article G for whether a foreign matter is present or whether a chip/crack is present, but not limited to this. In the case where the article G is wrapped in a sheet-like packaging material, the inspection unit 24 can also inspect a break of the packaging material, a seal failure of the packaging material (product in seal), or the like. In the case where the article G is accommodated in a package, the inspection unit 24 can perform a foreign matter confirmation inspection in the package, a missing part confirmation inspection, a number of accommodated articles confirmation inspection, a cavity confirmation inspection, or the like. The inspection unit 24 transmits the inspection results of the article G to the determination unit 25 and the storage unit 27.

The determination unit 25 determines whether the article G is non-defective on the basis of the inspection results received from the inspection unit 24. For example, the determination unit 25 determines whether a foreign matter is present in the article G, whether a chip/crack is present in the article G, or the like. The determination unit 25 transmits the determination results to the output unit 26 and the storage unit 27.

The output unit 26 outputs the determination results of the determination unit 25 to at least one of the units other than the control unit 10 in the X-ray inspection apparatus 1, and the apparatuses different from the X-ray inspection apparatus 1. This enables at least either of the X-ray inspection apparatus 1 and the apparatuses different from the X-ray inspection apparatus 1 (e.g., a sorting apparatus located downstream of the X-ray inspection apparatus 1) to perform the operation when the article G is defective. Other examples of the apparatuses different from the X-ray inspection apparatus 1 include, for example, the supply conveyor 51, the delivery conveyor 52, and a notification apparatus.

The storage unit 27 stores signals, data, or the like generated by the control unit 10. For example, the storage unit 27 stores detection results transmitted from the receiving unit 21, image data transmitted from the image generation unit 23, data related to inspection results transmitted from the inspection unit 24, and data related to determination results transmitted from the determination unit 25.

In the X-ray inspection apparatus 1 according to the present embodiment described above, when the mode switching unit 22 switches the operation mode from the normal mode in which the first power is supplied to the X-ray irradiation unit 6 to the power-saving mode in which the second power is supplied to the X-ray irradiation unit 6, the mode switching unit 22 changes the read frequency at which the image generation unit 23 reads the detection results. For example, since the read frequency of the detection results is reduced when the mode switching unit 22 switches the operation mode from the normal mode to the power-saving mode, the period (X-ray exposure period) can be extended during which each detecting element 11 is exposed to X-rays in the above-described read interval. This enables satisfactory detection results of the X-rays to be output from each detecting element 11 in the read interval, even when the output of the X-rays emitted from the X-ray irradiation unit 6 is weakened in the power-saving mode. Thus, by using the X-ray inspection apparatus 1 according to the present embodiment, a satisfactory inspection can be performed regardless of suppressing the output of X-rays.

In the present embodiment, the sensor unit 7 may detect X-rays by a photon counting method. In this case, the contrast of the image generated by the image generation unit 23 can be improved.

In the present embodiment, the second power may be a reciprocal multiple of a natural number of the first power. In this case, the power consumption of the X-ray inspection apparatus 1 can be satisfactorily reduced.

In the present embodiment, when switching the operation mode from the normal mode to the power-saving mode, the mode switching unit 22 may multiply the read frequency by the reciprocal of a natural number. In this case, the satisfactory detection results of the X-rays can be surely output from each detecting element 11.

In the present embodiment, when the normal mode is switched to the power-saving mode, the sensor unit 7 may change the number of operating detecting elements 11. In this case, since the detecting element 11 with an insufficient X-ray exposure time hardly exists, an unclear image is less likely to be generated.

In the present embodiment, when the normal mode is switched to the power-saving mode, the change rate of the read frequency may be the same as the ratio of the operating detecting elements 11 among the detecting elements 11. In this case, satisfactory detection results of the X-rays can be surely output from each operating detecting element 11.

The X-ray inspection apparatus 1 according to the present embodiment, includes the determination unit 25 that determines whether a foreign matter is present in the article G including a food, on the basis of the image. Thus, the determination unit 25 can satisfactorily determine whether a foreign matter is present even when the output of the X-ray is suppressed.

Although the embodiments of the disclosure have been described above, the disclosure is not necessarily limited to the above-described embodiments, and various modifications can be made without departing from the gist thereof. For example, in the above-described embodiments, the sensor unit is a device that can detect X-rays by a photon counting method, but not limited thereto. The detecting element included in the sensor unit may include at least a scintillator and a photodiode.

In the embodiment described above, the operation mode of the X-ray inspection apparatus includes one normal mode and one power-saving mode, but not limited to this. For example, the operation mode may include a plurality of normal modes. In each of the plurality of normal modes, for example, the power supplied to the X-ray irradiation unit is different from each other. The above operation mode may include a plurality of power-saving modes. In each of the plurality of power-saving modes, for example, at least one of the power supplied to the X-ray irradiation unit and the ratio of operating detecting elements is different from each other.

While preferred embodiments of the disclosure have been described above, it is to be understood that variations and modifications will be apparent to those skilled in the art without departing from the scope and spirit of the disclosure. The scope of the disclosure, therefore, is to be determined solely by the following claims.

The invention claimed is:

1. An X-ray inspection apparatus, comprising:

a conveying unit configured to convey an article;

an irradiation unit configured to irradiate the article conveyed by the conveying unit with X-rays;

a sensor unit in which detecting elements configured to detect the X-rays are arranged in a planar shape;

an image generation unit configured to read detection results output from at least some of the detecting elements and generate an image; and a mode switching unit configured to switch an operation mode between a first mode in which a first electric power is supplied to the irradiation unit and a second mode in which a second electric power less than the first electric power is supplied to the irradiation unit, wherein the mode switching unit changes, when switching the operation mode from the first mode to the second mode, a read frequency at which the image generation unit reads the detection results.

2. The X-ray inspection apparatus according to claim 1, wherein the sensor unit is configured to detect the X-rays by a photon counting method.

3. The X-ray inspection apparatus according to claim 1, wherein the second electric power is any multiple less than 1 time of the first power.

4. The X-ray inspection apparatus according to claim 3, wherein when switching the operation mode from the first mode to the second mode, the mode switching unit multiplies the read frequency by any multiple less than 1 time.

5. The X-ray inspection apparatus according to claim 1, wherein when the first mode is switched to the second mode, the sensor unit changes the number of detecting elements that operate among the detecting elements.

6. The X-ray inspection apparatus according to claim 5, wherein when the first mode is switched to the second mode, a change rate of the read frequency is the same as a ratio of the detecting elements that operate among the detecting elements.

7. The X-ray inspection apparatus according to claim 1, further comprising a determination unit configured to determine whether a foreign matter is present in the article including a food, on the basis of the image.

* * * * *